United States Patent [19]

Kim et al.

[11] Patent Number: 5,075,446

[45] Date of Patent: Dec. 24, 1991

[54] SYNTHESIS OF TETRAHYDRO-2-FURYLATED PYRIMIDINE DERIVATIVES

[75] Inventors: Yong H. Kim; Chun H. Lee, both of Seoul, Rep. of Korea

[73] Assignee: Korea Advanced Institute of Science & Technology, Seoul, Rep. of Korea

[21] Appl. No.: 598,892

[22] Filed: Oct. 12, 1990

[30] Foreign Application Priority Data

Dec. 29, 1989 [KR] Rep. of Korea ............... 1989-20247

[51] Int. Cl.$^5$ ........................................... C07D 407/04

[52] U.S. Cl. ................................... 544/316; 544/317; 544/318

[58] Field of Search ..................... 544/316, 317, 318

*Primary Examiner*—John M. Ford
*Attorney, Agent, or Firm*—Michael N. Meller

[57] ABSTRACT

The synthesis of 1-(tetrahydro-2-furyl) pyrimidine derivatives in good yields by the reaction of trimethylsilylated pyrimidine bases with 2-acetoxytetrahydrofuran using a catalytic amount of cesium chloride in acetonitrile under mild conditions is described.

3 Claims, No Drawings

SYNTHESIS OF TETRAHYDRO-2-FURYLATED PYRIMIDINE DERIVATIVES

FIELD OF THE INVENTION

This invention relates to a novel synthesis of tetrahydro-2-furylated pyrimidine derivatives of the formulas I and II, i.e.,

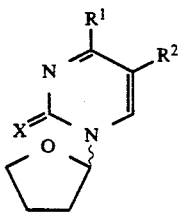

wherein
X is oxygen or sulfur,
R¹ is hydroxy,amino or methyl and or amino
R² is fluorine, hydrogen, methyl with the proviso that when X is oxygen,
R¹ is hydroxyand R² is fluorine,
R¹ is hydroxy and R² is hydrogen,
R¹ is an amino group and R² is hydrogen,
R¹ is hydroxy and R² is a methyl group,
or R¹ ishydroxy and R² is an amino group;
and wben X is sulfur.
R¹ ishydroxy and R² is a methyl group, or R¹ is a methyl group and R² is hydrogen; or

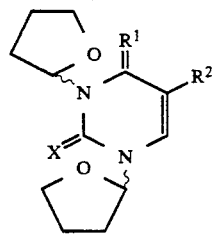

wherein
X is oxygen, R¹ is oxygen
and R² is hydrogen or methyl.

In the previously reported methods for the synthesis of tetrahydro-2-furylated pyrimidine derivatives, C. W. Noell et al. in *J. Heterocycl. Chem.*, 25-28 (1968), describe the condensation of pyrimidine bases with 2-substituted tetrahydrofuran in the presence of Na₂CO₃. M. Yasumoto et al., in *J. Med. Chem.*. 21(8) 738-741 (1978), describe the use of SnCl₄ as a Friedel-Crafts catalyst. Mikmi describes the use of the AlCl₃ and TiCl₃ as catalysts (Japan Kokai Nos. 77-139076 and 77-83,386). While these known methods described above are quite efficient, problems still remain as to how to increase yields and improve reaction conditions and procedures.

Therefore, an object of the present invention is to provide new and improved methods for the synthesis of tetrahydro-2-furylated pyrimidine derivatives.

According to the invention, the pure compound(I) is synthesized in high yields by the condensation of a pyrimidine of the general formula (III),

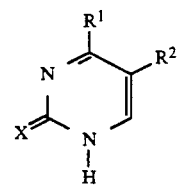

wherein
X is oxygen or sulfur, R¹ is hydroxy, amino or methyl and R² is fluorine, hydrogen, bromine, methyl or amino with the proviso that when X is oxygen and R¹ is hydroxy,
R² is fluorine, hydrogen, bromine, methyl or amino, and wherein X is oxygen and R¹ is amino, R² is hydrogen;
when X is sulfur, R¹ is oxygen and R² is methyl, or R¹ is methyl and R² is hydrogen, With 2-acetoxytetrahydrofuran (Thf-OAc) of the formula (IV),

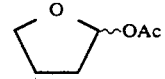

using a new catalyst of cesium chloride in organic solvents under mild conditions.

The detailed applicants' method for the condensation is as follows: firstly, the pyrimidine base (III) is silylated by hexamethyldisilazane (HMDS) in the presence of a catalytic amount of ammonium sulfate and is followed by concentration of the reacted solution; the concentrate is dissolved in dry acetonitrile; then to the solution is added cesium chloride (0.1 equivalent amount for the base) and 2-acetoxytetrahydrofuran (Thf-OAc, IV, 1.2-1.5 equivalent amount for the base) at room temperature or up to about 50°-55° C. and stirring for several hours to afford the corresponding pyrimidine derivatives (I) in high yields together with a minor amount of the compound (II) which can be readily separated.

The use of cesium chloride gives higher yields under mild conditions. The new reactants of the present invention using cesium chloride are easier to handle, and simpler to work up than those using other Lewis acid catalysts.

Furthermore, the condensation by cesium chloride shows the regioselectivity for the alkylation at the N¹-position of pyrimidines. It is assumed that 2-acetoxytetrahydrofuran is activated first by cesium chloride through the interaction between the cesium cation and the tetrahydrofuran ether oxygen to promote the carbonium electrophilicity at the C²-position. The best yield is obtained using the proper amount of 2-acetoxytetrahydrofuran. When the relative amount of Thf-OAc and the reaction temperature are increased, the reaction time is reduced. However the compound (II), overalkylated at N³-position of pyrimidine, is also obtained together with the compound (I). Thus, it is important to use the proper amount of (III) to obtain (I) versus (II) as described in the experimental section.

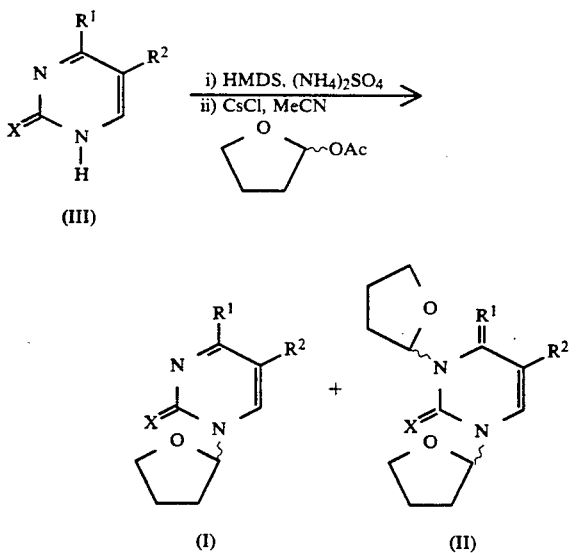

Typical compounds which may be prepared by the novel synthesis of the present invention include, for example,
1-(tetrahydro-2-furyl)-5-fluorouracil,
1-(tetrahydro-2-furyl)-uracil,
1,3-bis(tetrahydro-2-furyl)-uracil,
1-(tetrahydro-2-furyl)-cytosine,
1-(tetrahydro-2-furyl)-5-bromouracil,
1-(tetrahydro-2-furyl)-5-aminouracil,
1-(tetrahydro-2-furyl)-thymine,
1,3-bis-(tetrahydro-2-furyl)-thymine,
5-methyl-1-(tetrahydro-2-furyl)-2-thiouracil, and,
1-(tetrahydro-2-furyl)-4-methyl-2-thiopyrimidine.

In particular, the 1-(tetrahydro-2-furyl)-5-fluorouracil, named Ftorafur or FT-207, is an effective cancer therapeutic agent and can be given orally and shows relatively low toxicity.

The following examples of this invention are illustrated, but the scope of this invention is not limited to the examples described here.

EXPERIMENTAL SECTION

Trimethylsilylation of pyrimidine

A mixture of pyrimidine base (2 mmol) and hexamethyldisilazane (HMDS; 10 ml) was heated at reflux for 3-6 hr in the presence of ammonium sulfate (5 mg) under anhydrous conditions. The resulting clear solution was concentrated in vacuo and immediately used for the subsequent reactions as noted in the following examples:

EXAMPLE 1

1-(Tetrahydro-2-furyl)-5-fluorouracil (Ftorafur)

To a solution of the trimethylsilylated 5-fluorouracil (2 mmol) in dry MeCN (5 ml) was added CsCl (35 mg, 0.2 mmol) and Thf-OAc (390 mg, 3 mmol) and stirred for 3 hours at room temperature. After the reaction was completed, the reaction mixture was concentrated and the residue was extracted with $CH_2Cl_2$ (30 ml×3)-water (20 ml). The combined organic layer was concentrated and the residue was crystallized in EtOH to obtain the title compound (346 mg, 87% yield).

mp=165°-167° C.; $^1H$ NMR (CDCl$_3$)δ2.2 (m, 4H), 4.2 (m, 2H), 6.1 (t, 1H), 7.6 (d, 1H), 10.2 (brs, 1H).

EXAMPLE 2

1-(Tetrahydro-2-furyl) uracil and 1,3-bis(tetrahydro-2-furyl) uracil

A mixture of trimethylsilylated uracil (2 mmol), Thf-OAc (3mmol) and CsCl (35 mg) was stirred in dry MeCN (5 ml) for 3 hours at room temperature. The residue was chromatographed on silica gel to obtain the two title compounds.

1-(Tetrahydro-2-furyl) uracil (78% yield); $^1H$ NMR (CDCl$_3$)δ2.2 (m, 4H), 4.2 (m, 2H), 5.9-7.9 (dd, 2H).
1,3-Bis(tetrahydro-2-furyl) uracil (20% yield); $^1H$ NMR (CDCl$_3$)δ2.2 (m, 8H), 4.2 (m, 4H), 6.0 (t, 1H), 6.7 (t, 1H), 5.8-7.8 (dd, 2H).

EXAMPLE 3

1-(Tetrahydro-2-furyl) cytosine

A mixture of trimethylsilylated cytosine (2 mmol), Thf-OAc (3 mmol) and CsCl (0.2 mmol) was stirred in dry MeCN (5 ml) for 5 hours at room temperature. The reaction mixture was purified by chromatography using silica gel to obtain the title compound (83% yield). mp=193°-195° C.; $^1H$ NMR (DMSO-d$_6$)δ 2.2 (m, 4H), 4.2 (m, 2H), 6.1 (t, 1H), 6.9 (s, 2H), 6.0-7.5 (dd, 2H).

EXAMPLE 4

1-(Tetrahydro-2-furyl)-5-aminouracil

A mixture of trimethylsilylated 5-aminouracil (2 mmol), Thf-OAc (3 mmol) and CsCl (0.2 mmol) was stirred in dry MeCN (5 ml) for 4 hours at room temperature. The residue was purified by use of a silica gel column to obtain the title compound (50% yield). $^1H$ NMR (DMSO-d$_6$)δ 2.2 (m, 4H), 4.2 (m, 2H), 6.2 (t, 1H), 7.0 (s, 1H); Mass (m/z) 197 (M+).

EXAMPLE 6

1-(Tetrahydro-2-furyl) thymine and 1,3-bis(tetrahydro-2-furyl) thymine

A mixture of trimethylsilylated thymine (2 mmol), Thf-OAc (2.4 mmol) and CsCl (0.2 mmol) was stirred in dry MeCN (5 ml) for 3 hours at 50°-55° C. The reaction mixture was purified by the chromatography on silica gel to obtain the two title compounds. 1-(Tetrahydro-2-furyl) thymine (73% yield); mp=183°-185° C.; $^1H$ NMR (DMSO-d$_6$)δ 2.1 (s, 3H), 2.2 (m, 4H), 4.2 (m, 2H), 6.6 (t, 1H), 7.5 (s, 1H).

1,3-Bis(tetrahydro-2-furyl) thymine (22% yield); $^1H$ NMR (CDCl$_3$)δ 2.1 (s, 3H), 2.2 (m, 8H), 4.2 (m, 4H), 6.0 (t, 1H), 6.7 (t, 1H), 8.2 (s, 1H).

EXAMPLE 7

5-Methyl-1-(tetrahydro-2-furyl)-2-thiouracil

A mixture of trimethylsilylated 5-methyl-2-thiouracil (2 mmol), Thf-OAc. (3 mmol) and CsCl (0.2 mmol) was stirred in dry MeCN (5 ml) for 3 hours at 50°-55° C. The reaction mixture was chromatographed on silica gel to obtain the title compound (96% yield).

$^1H$ NMR (DMSO-d$_6$)δ 2.0 (s, 3H), 2.2 (m, 4H), 4.2 (m, 2H), 6.6 (t, 1H), 7.5 (s, 1H), 12.5 (brs, 1H); Mass (m/z) 212 (M+).

EXAMPLE 8

1-(Tetrahydro-2-furyl)-4-methyl-2-thioovrimidine

A mixture of trimethylsilylated 4-methyl-2-thiopyrimidine (1 mmol), Thf-OAc (1.5 mmol) and CsCl (0.1 mmol) was stirred in dry MeCN (3 ml) at 20° C. for 1.5 hours. The reaction mixture was purified by chromatography on silica gel to obtain the title compound (91% yield).

$^1$H NMR (CDCl$_3$)δ 2.0(m, 4H), 2.5 (s, 3H), 4.0 (m, 2H), 6.5 (t, 1H), 6.9–8.5 (dd, 2H).

WHAT IS CLAIMED IS:

1. A process of preparing tetrahydro-2-furylated pyrimidine derivatives of the formulas (I) and (II), wherein in formula

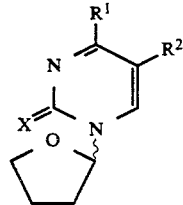
(I)

wherein

X is selected from the group consisting of oxygen and sulfur,

R$^1$ is selected from the group consisting of hydroxy amino and methyl, and

R$^2$ is selected from the group consisting of fluorine, hydrogen, methyl and amino with the proviso that when X is oxygen, R$^1$ is hydroxy and R$^2$ is fluorine, R$^1$ ishydroxy and R$^2$ is a methyl group, R$^1$ is hydroxy and R$^2$ is an amino group; and or R$^1$ is hydroxy and R$^2$ is an amino group; and when X is sulfur, R$^1$ is hydroxy and R$^2$ is a methyl qroup, or R$^1$ is a methyl group and R$^2$ is hydrogen; and in formula (II):

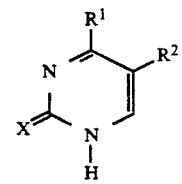
(II)

wherein

X is oxygen, R$^1$ is oxygen and R$^2$ is selected from the group consisting of hydrogen and methyl, which comprises the condensation of a pyrimidine of formula (III):

(III)

wherein

X is selected from the group consisting of oxygen and sulfur,

R$^1$ is selected from the group consisting of hydroxy amino and methyl and R$^2$ is selected from the group consisting of fluorine, hydrogen, bromine, methyl and amino with the proviso that when X is oxygen and R$^1$ is hydroxy, R$^2$ is selected from the group consisting of fluorine, hydrogen, bromine, methyl and amino, and wherein X is oxygen and R$^1$ is amine, R$^2$ is hydrogen;

and when X is sulfur,

R$^1$ is hydroxy and R$^2$ is methyl, or R$^1$ is methyl and R$^2$ is hydrogen with 2-acetoxytetrahydrofuran of the formula (IV):

(IV)

in the presence of a catalytic amount of cesium chloride in an organic solvent under mild conditions.

2. The process according to claim 1, where cesium chloride is added as a 0.1 molar equivalent amount of the pyrimidine (III).

3. The process according to claim 1, where the organic solvent is acetonitrile.

* * * * *